United States Patent [19]

Fukuda

[11] Patent Number: 5,245,935
[45] Date of Patent: Sep. 21, 1993

[54] EQUIPMENT FOR MELTING USED INJECTION NEEDLES

[75] Inventor: Tadahiro Fukuda, Tokyo, Japan
[73] Assignee: ASC Co., Ltd., Tokyo, Japan
[21] Appl. No.: 972,210
[22] Filed: Nov. 3, 1992

[30] Foreign Application Priority Data

May 7, 1992 [JP] Japan .................. 4-041766[U]

[51] Int. Cl.$^5$ .................................. F23G 5/00
[52] U.S. Cl. ......................... 110/250; 128/919; 219/68
[58] Field of Search ............. 110/250, 346; 219/68; 128/919

[56] References Cited

U.S. PATENT DOCUMENTS

| | | | |
|---|---|---|---|
| 4,965,426 | 10/1990 | Colombo | 219/68 |
| 5,076,178 | 12/1991 | Kohl et al. | 110/250 |
| 5,091,621 | 2/1992 | Butler | 219/68 |
| 5,166,488 | 11/1992 | Peppard | 219/68 X |
| 5,212,362 | 5/1993 | Burden et al. | 219/68 X |

Primary Examiner—Edward G. Favors
Attorney, Agent, or Firm—Dickinson, Wright, Moon, Van Dusen & Freeman

[57] ABSTRACT

Equipment for melting a used injection needle includes a pair of movable contacts (2) and a fixed contact (3) between which electric voltage is applied. A short-circuit detector (4), determines when the movable contacts (2) and the fixed contact (3) are short-circuited by a used injection needle (9), and a timer (5) produces a signal during the period in which the short-circuit detector (4) produces a signal. An electromagnet drives the movable contacts (2) together to secure the used injection needle (9) to decrease the contact resistance between the movable contacts (2) and the used injection needle (9) and to allow a large electric current to flow in the used injection needle (9) in a stable manner.

8 Claims, 4 Drawing Sheets

EQUIPMENT FOR MELTING USED INJECTION NEEDLES

TECHNICAL FIELD

This invention relates to equipment for melting a used injection needle. More specifically, this invention relates to equipment capable of melting a used injection needle to the root or base thereof and making the melted end dull.

BACKGROUND OF THE INVENTION

To prevent the transmission of diseases through microorganisms contained in the blood remaining in or outside used injection needles, the points of needles to be discarded are dulled so that they can not cause harm to human bodies they contact.

In the prior art, equipment is known that curls the point of a used injection needle or melts the tip of a used injection needle. An example of a known device for melting used injection needles will be described below with reference to FIG. 1. The diameter of usual injection needles varies between 0.5 mm and 2 mm. As shown in FIG. 1, a pair of fixed contacts 23 and 24 are supported by a box 82 for receiving a used injection needle. The distance between the fixed contacts 23 and 24 is approximately 0.5 mm, as shown in the figure. A third fixed contact 32 is arranged facing the gap between the first and second fixed contacts 23 and 24. An electric voltage is applied between the first fixed contact 23 and the third fixed contact 32.

When the foregoing equipment is employed, a used injection needle 9 is inserted between the first and second contacts 23 and 24 and is moved in the direction of arrow A until the lower end of the used injection needle 9 engages the third fixed contact 32 while the base of the used injection needle 9 is in contact with the first and second fixed contacts. Keeping this position, the used injection needle 9 is further pushed in the direction of the arrow A to allow an electric current to flow in the used injection needle 9 and to melt particularly the portion of the used injection needle 9 contacting the third fixed contact 32.

The first and second contacts 23 and 24 have the shape shown in FIG. 1 to facilitate insertion of a used injection needle 9. The top surface of the third fixed contact 32 is inclined to allow melted scrap to fall easily into a scrap box 31.

Protective cover 83 is arranged over the first and second fixed contacts 23 and 24 to provide safety, and this makes it difficult to see whether the base of a used injection needle 9 is in contact with the first and second fixed contacts 23 and 24. Therefore, the contact of the base of a used injection needle 9 and the first and second fixed contacts 23 and 24 is often incomplete resulting in the drawback that the electric current flowing in the used injection needle 9 is intermittent. This causes incomplete heating of the lower end of the used injection needle 9 and allows the lower end of the used injection needle 9 to curl, as shown in FIG. 3 (a) or to be deformed, as shown in FIG. 3 (b). It is difficult with the known devices to melt the used injection needle 9 substantially to the base thereof to make the end dull, as shown in FIG. 2.

The object of this invention is to provide equipment for melting a used injection needle, the equipment having the following advantages :

1. It is easy to insert a used injection needle to a position at which melting treatment is conducted.
2. The contact between the used injection needle and the fixed contacts is complete during melting whereby the used injection needle is melted substantially to the base and the point of the used injection needle is made dull, as shown in FIG. 5.

SUMMARY OF THE INVENTION

The foregoing object is achieved by the equipment for melting a used injection needle in accordance with this invention as described below:

The first embodiment of the invention provides:

a pair of movable contacts (2) for supporting the base of a used injection needle therebetween, a holder (8) for supporting each of the movable contacts (2) to allow the movable contacts (2) to engage each other and to be separated from each other elastically, a fixed contact (3) facing the movable contacts (2) to engage the lower end of the used injection needle, an elastic body (7) for urging the two movable parts of holder (8) toward each other to cause the movable contacts (2) to be in contact with each other, a contacts-short-circuit-detecting-sensor (4), which operates when the voltage between the movable contacts (2) and the fixed contact (3) is less than a predetermined value, a timer (5), which starts timing in response to the operation of the contacts-short-circuit-detecting-sensor (4), and an electromagnet (6) for pulling the parts of holder (8) together to cause the movable contacts (2) to contact the base of needle (9) during the period in which the timer (5) continues timing operation.

Fixed contact (3) is preferably made of tungsten to increase the temperature of the fixed contact (3) and cause melting from the lower end of the used injection needle. As a result, it is possible to obtain the shape of the melted used injection needle shown in FIG. 2.

Further, the angle between the top surface of the fixed contact (3) and the used injection needle is preferably 45 degrees-60 degrees to prevent the lower end of the used injection needle from curling as shown in FIG. 3 (a) and to expedite dropping of the scrap from the fixed contact (3).

The second embodiment of the invention provides:

a first fixed contact (21), a movable arm (81), which is hinged at one end and which supports a movable contact (22) at the other end for contacting the first fixed contact (21) and holding the base of a used injection needle therebetween, a second fixed contact (3) facing the movable contact (22) for engaging the lower end of the used injection needle, an elastic body (7) for driving the arm (81) to pull the movable contact (22) toward the first fixed contact (21), a contacts-short-circuit-detecting-sensor (4), which operates when the voltage between the first fixed contact (21) and the second fixed contact (3) is less than a pre-determined value, a timer (5) which starts timing in response to the operation of the contacts-short-circuit-detecting-sensor (4), and an electromagnet (6) for driving the arm (81) to pull the movable contact (22) toward the first fixed contact (21) during the period in which the timer (5) continues timing operation.

The second fixed contact (3) is preferably made of tungsten to increase the temperature of the second fixed contact (3) and cause melting from the lower end of the used injection needle. As a result, it is possible to obtain the shape of the melted used injection needle shown in FIG. 2.

Further, the angle between the top surface of the second fixed contact (3) and the used injection needle is preferably 45 degrees–60 degrees to prevent the lower end of the used injection needle from curling as shown in FIG. 3 (a) and to expedite dropping of the scrap from the second fixed contact (3).

DETAILED DESCRIPTION OF PREFERRED EMBODIMENTS

First Embodiment

Figure 3:
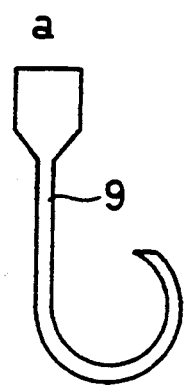
FIGS. 3 (a) and 3 (b) show used injection needles after being treated by equipment for melting a used injection needle available in the prior art.
Figure 3:
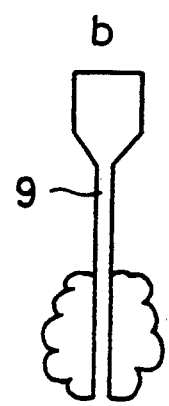
Figure 4:
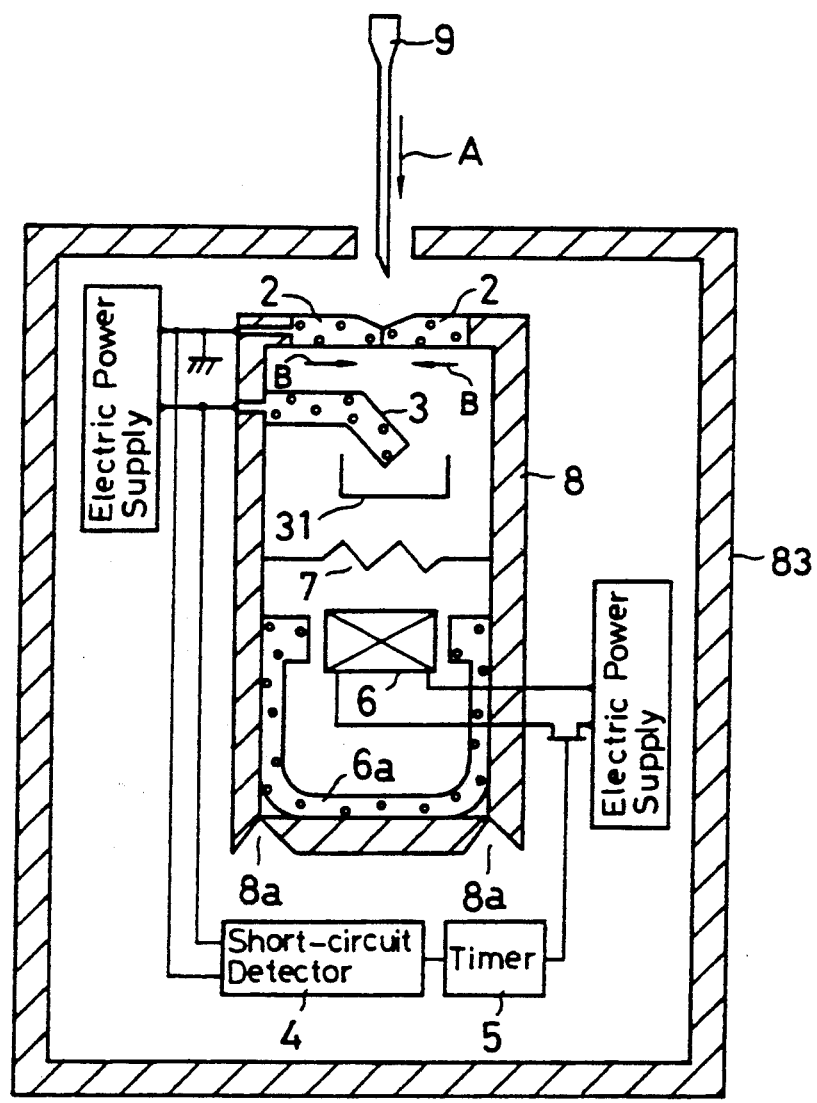
FIG. 4 is a vertical cross section of a first embodiment of equipment for melting a used injection needle in accordance with this invention.
Figure 5:
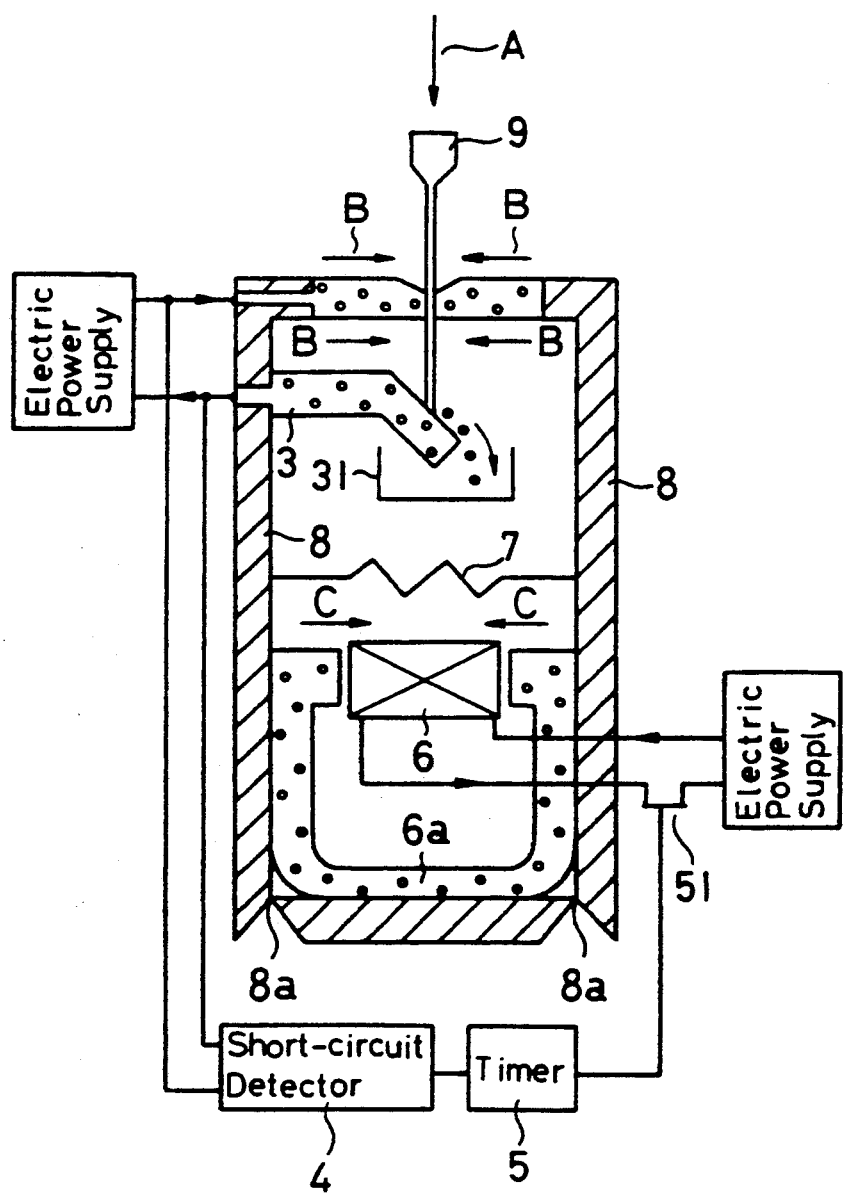
FIG. 5 illustrates operation of the equipment shown in FIG. 4.

FIGS. 4 and 5 illustrate a first embodiment of the invention. Referring to FIG. 4, each contact of a pair of movable contacts 2 is supported by a holder 8 which elastically supports the movable contacts 2 to allow them to engage each other or to be separated. This holder 8 is made of an elastic material and includes hinges at 8a. The holder 8 also supports a fixed contact 3. When a used injection needle 9 is inserted in the direction of arrow A to be treated, the lower end of the used injection needle 9 engages the fixed contact 3, and the movable contact 2 and the fixed contact 3 are short-circuited The fixed contact 3 is made of tungsten in this embodiment to increase the temperature of the lower end of the needle. The angle between the top surface of the fixed contact 3 and the used injection needle 9 is selected to be in the range of 45 degrees through 60 degrees for preventing curling of the lower end of the used injection needle, as shown in FIG. 3 (a) and to allow the scrap to drop into scrap box 31. An elastic body 7 drives the movable contacts 2 toward each other. The force in this embodiment applied by elastic body 7 is approximately 10 grams weight, which allows easy insertion of the used injection needle 9.

An electric voltage is applied between the movable contact 2 and the fixed contact 3. The voltage is 6 volts in this embodiment. For the safety's sake, the movable contact 2 is grounded and the voltage may be AC or DC. Further, the electric power supply may be installed inside or outside protection box 83. The capacity of the electric power supply is 300W in this embodiment. The intensity of electric current flowing in an ordinary injection needle varies from 30A to 70A.

The contacts-short-circuit-detecting-sensor 4 operates when the movable contacts 2 and the fixed contact 3 are short-circuited by a used injection needle 9.

A timer 5 continues outputting a signal for a predetermined period in response to an operation of the contacts-short-circuit-detecting-sensor 4. If the contacts-short-circuit-detecting-sensor 4 operates a number of times, the last operation supersedes the previous ones, and the timer continues outputting a signal for a predetermined period commencing with the last operation of the contacts-short-circuit-detecting-sensor 4. Therefore, if the connection between the movable contacts 2 and the fixed contact 3 is discontinued, for example, by chattering of the movable contacts 2, the timer 5 provides a signal for a longer period.

An electromagnet 6 is driven by a switch 51 which operates in response to the signal of the timer 5. Thus, the electromagnet 6 continues operation during the period 17 which the timer 5 continues to provide a signal. Magnetic flux passes through a magnetic pass 6a during the period in which the electromagnet 6 operates to pull the pair of movable contacts 2 together. The driving force of the electromagnet is approximately 150–200 grams weight in this embodiment. The equipment is housed in a protection box 83.

Figure 1:
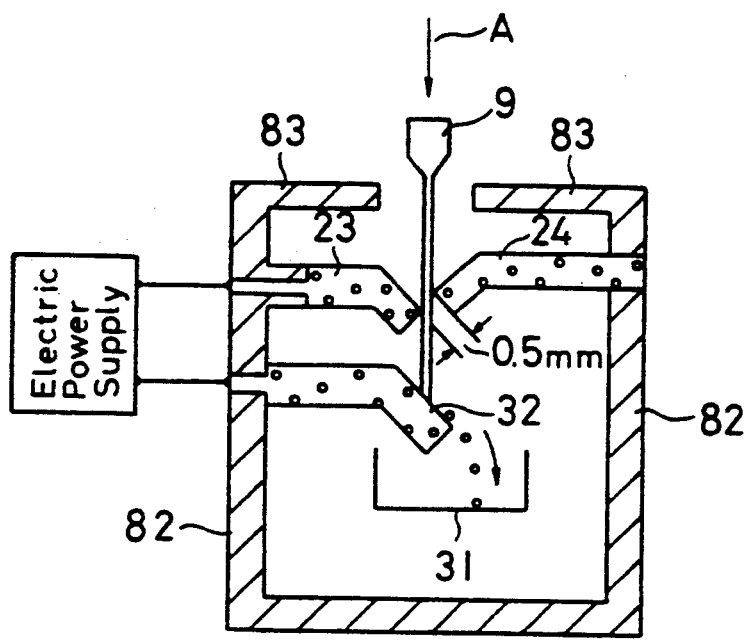
FIG. 1 is a vertical cross section of known equipment for melting a used injection needle.
Figure 2:
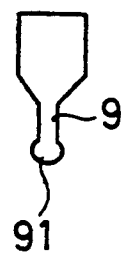
FIG. 2 shows a used injection needle after being treated by the equipment for melting a used injection needle of this invention.

Referring to FIG. 5, a used injection needle 9 is easily pushed down in the direction of the arrow A and inserted between the pair of movable contacts 2 because the force pulling the pair of movable contacts 2 together is very small, e.g., 10 grams weight, until the lower end of the used injection needle 9 contacts the fixed contact 3. When the lower end of the used injection needle 9 contacts the fixed contact 3, however, the electromagnet 6 strongly pulls the holder 8 in the direction of an arrow C with the force of approximately 150–200 grams weight. As a result, the pair of movable contacts 2 strongly contact with each other to decrease the electric resistance of this portion, resultantly allowing an electric current of 30A–70A in the used injection needle 9 and increasing the temperature thereof up to 2000 degrees C. As a result, when a used injection needle 9 is pushed down in the direction of the arrow A, it melts from the lower end thereof to the neighborhood of the base within 1–2 seconds, and the scrap readily drops into the scrap box 31. As a result, the shape of the point 91 of the used injection needle 9 is made dull in the neighborhood of the base, as shown in FIG. 2.

Second Embodiment

Figure 6:
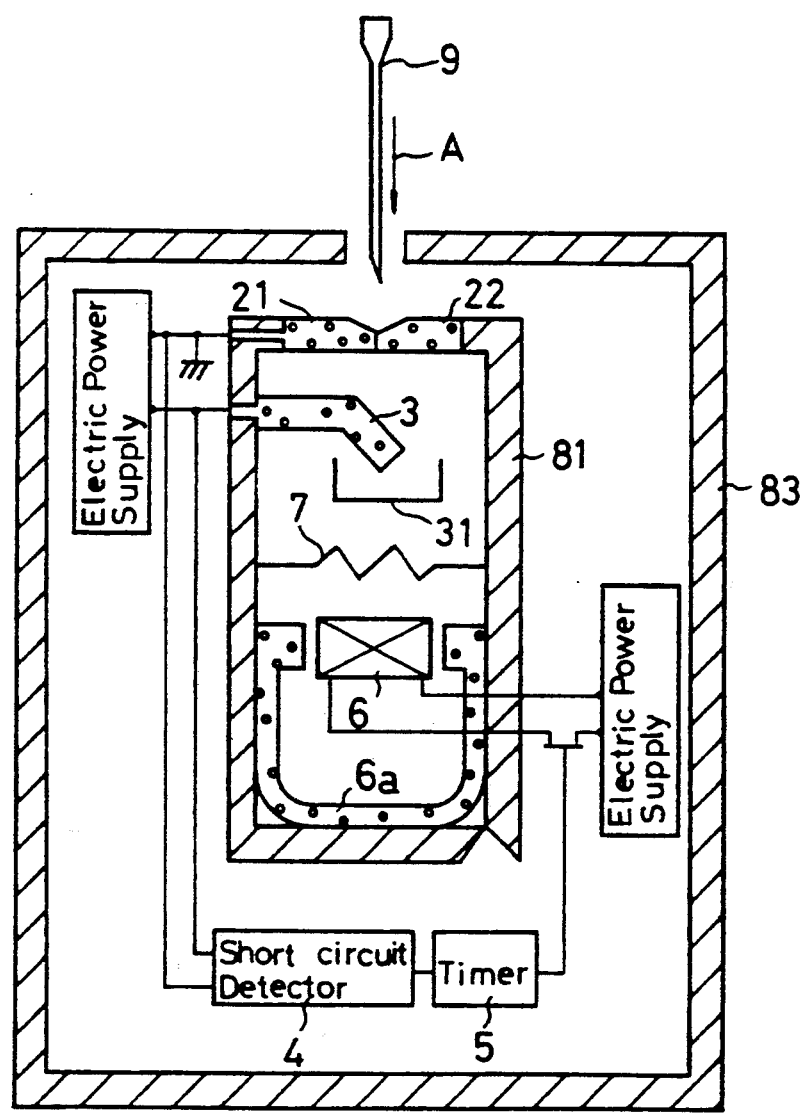
FIG. 6 is a vertical cross section of a second embodiment of equipment for melting a used injection needle in accordance with this invention.

Referring to FIG. 6, the second embodiment differs from the first embodiment in the following points.

1. The pair of movable contacts 2 of the first embodiment is changed in the second embodiment to be a combination of a first fixed contact 21 and a movable contact 22.

2. The fixed contact 3 of the first embodiment is changed in the second embodiment to be a second fixed contact.

3. The holder 8 which supports each the movable contacts 2 is changed in the second embodiment to have a pivotal arm 81 with one end hinged and the other end supporting the movable contact 22.

Although both embodiments perform similar function, possibly unstable structure of the pair of movable contacts 2 of the first embodiment is avoided in the second embodiment by providing a first fixed contact 21 and a movable contact 22. As a result, the second embodiment may be more convenient rather than the first embodiment.

It will be appreciated that this invention successfully provides equipment for melting injection needles having the following advantages :

1. A used injection needle can be easily inserted between each a pair of movable contacts or between a first fixed contact and a movable contact.

2. Once electric current begins to flow in the used injection needle, the resistance between the movable contact and the used injection needle becomes low and stable, thus allowing the used injection needle to melt from the lower end to the neighborhood of the base to make the point dull or harmless to the human body.

What is claimed is :

1. Apparatus for melting a used injection needle comprising:

a pair of relatively movable contacts (2) for supporting the base of said used injection needle therebetween, a holder (8) for supporting each of said movable contacts (2) and allowing said movable contacts (2) to engage each other and to separate from each other elastically, a fixed contact (3) facing said movable contacts (2) for engaging the lower end of said used injection needle, elastic means (7) for elastically urging said holder (8) in the direction to cause said movable contacts (2) to contact each other, a contacts-short-circuit-detecting-sensor (4) which produces an output signal when the voltage between said movable contacts (2) and said fixed contact (3) is less than a predetermined value, a timer (5) which starts timing operation in response to the output signal of said contacts-short-circuit-detecting-sensor (4), and an electromagnet (6) for driving said holder (8) in the direction to cause each of said movable contacts (2) to contact during the period in which said timer (5) continues timing operation.

2. Apparatus for melting a used injection needle in accordance with claim 1, wherein said fixed contact (3) is made of tungsten.

3. Apparatus for melting a used injection needle in accordance with claim 1 wherein the angle between an upper surface of said fixed contact (3) and said used injection needle is 45 degrees-60 degrees.

4. Apparatus for melting a used injection needle in accordance with claim 2 wherein the angle between an upper surface of said fixed contact (3) and said used injection needle is 45 degrees-60 degrees.

5. Apparatus for melting a used injection needle comprising:

a first fixed contact (21), a movable arm (81) supporting a movable contact (22) for holding the base of a used injection needle therebetween, a second fixed contact (3) facing said movable contact (22) for engaging the lower end of said used injection needle, elastic means (7) for driving said movable arm (81) to cause said movable contact (22) to engage said first fixed contact (21), a contacts-short-circuit-detecting-sensor (4) for providing an output signal when the voltage between said first fixed contact (21) and said second fixed contact (3) is less than a predetermined value, a timer (5) which starts a timing operation in response to said output signal, and an electromagnet (6) for driving said arm (81) in the direction to contact said movable contact (22) with said first fixed contact (21) during the period in which said timer (5) continues said timing operation.

6. Apparatus for melting a used injection needle in accordance with claim 5, wherein said second fixed contact (3) is made of tungsten.

7. Apparatus for melting a used injection needle in accordance with claim 5 wherein the angle between an upper surface of said second fixed contact (3) and said used injection needle is 45 degrees-60 degrees.

8. Apparatus for melting a used injection needle in accordance with claim 6 wherein the angle between an upper surface of said fixed contact (3) and said used injection needle is 45 degrees-60 degrees.

* * * * *